US00RE34816E

United States Patent [19]

Poettgen

[11] E Patent Number: Re. 34,816

[45] Reissued Date of Patent: Jan. 3, 1995

[54] REFLECTIVE SURGICAL DRAPE

[75] Inventor: Robert J. Poettgen, Arlington, Tex.

[73] Assignee: O.R. Concepts, Inc., Roanoke, Tex.

[21] Appl. No.: 658,170

[22] Filed: Feb. 20, 1991

Related U.S. Patent Documents

Reissue of:

[64] Patent No.: 4,765,323
Issued: Aug. 23, 1988
Appl. No.: 890,403
Filed: Jul. 25, 1986

[51] Int. Cl.[6] ..... B32B 15/08

[52] U.S. Cl. ..... 128/849; 428/285; 428/461

[58] Field of Search ..... 128/849–856, 128/155, 156; 2/DIG. 7, 69, 69.5; 5/482–484, 500, 502; 428/285, 286, 461, 516

[56] References Cited

U.S. PATENT DOCUMENTS

| | | |
|---|---|---|
| 2,897,109 | 7/1959 | Voigtman . |
| 3,538,912 | 11/1970 | Becker, III . |
| 3,539,374 | 11/1970 | Isaacson . |
| 3,561,440 | 2/1971 | Bayer et al. . |
| 3,565,067 | 2/1971 | Bayer et al. . |
| 3,589,975 | 6/1971 | Andrews et al. . |
| 3,665,918 | 5/1972 | Lindquist et al. . |
| 3,667,458 | 6/1972 | Krebs . |
| 3,718,528 | 2/1973 | Bergstrom . |
| 3,809,077 | 5/1974 | Hansen . |
| 3,813,315 | 5/1974 | Valyi . |
| 3,934,582 | 1/1976 | Gorrie . |
| 4,018,646 | 4/1977 | Ruffo et al. . |
| 4,023,969 | 5/1977 | Sheridon . |
| 4,334,529 | 6/1982 | Wirth et al. . |
| 4,414,968 | 11/1983 | Amin . |
| 4,433,019 | 2/1984 | Chumbley . |
| 4,433,026 | 2/1984 | Molde . |
| 4,471,769 | 9/1984 | Lockhart . |
| 4,476,593 | 10/1984 | Fanselow et al. . |
| 4,479,492 | 10/1984 | Singer . |
| 4,508,776 | 4/1985 | Smith . |
| 4,524,767 | 6/1985 | Glassman . |
| 4,637,947 | 1/1987 | Maekawa et al. . |
| 4,715,366 | 12/1987 | Teeple . |

FOREIGN PATENT DOCUMENTS

| | | |
|---|---|---|
| 1263071 | 2/1972 | United Kingdom . |
| WO85/03216 | 8/1985 | WIPO . |

OTHER PUBLICATIONS

Dyde et al., *Thorax*, 25: 355 (1970).
Lever Brothers Company Purchase Specification No. 587–433–013 dated Jul. 20, 1984.
Jen–Coat Inc. letter dated Jun. 24, 1986.
Jen–Coat Pricing for C. H. Dexter dated Aug. 15, 1986.
TECHStyles letter dated Nov. 5, 1990.
Bourke et al., *Anesthesiology*, 60: 151 (1984).
Radford et al., *Br. J. Anaesth.*, 51: 237 (1979).
Cundy, *Br. J. Anaesth.*, 52: 359 (1980).

*Primary Examiner*—Robert A. Hafer
*Assistant Examiner*—Sam Rimell
*Attorney, Agent, or Firm*—Randall C. Brown

[57] ABSTRACT

A new, lightweight reflective surgical drape which is effective in reducing the rate of heat loss in human patients during a variety of surgical procedures is disclosed. The drape comprises a core layer of non-conductive aluminum and a first and second adjacent layer of a thermoplastic material. A non-woven layer of absorbent material is attached to either the first or second adjacent layer of thermoplastic material.

In a preferred embodiment, the drape of the present invention comprises a first layer of non-conductive aluminum and a second layer of a thermoplastic material. A third layer of non-woven absorbent material is attached to the first layer of non-conductive aluminum.

39 Claims, 2 Drawing Sheets

REFLECTIVE SURGICAL DRAPE

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to a new, lightweight reflective surgical drape which is effective in reducing the rate of heat loss in human patients during a variety of surgical procedures.

2. Description of the Prior Art

Heat loss in human patients during surgical procedures often leads to intraoperative hypothermia. Such hypothermia is caused in part by anesthesia which depresses the thermal regulating centers in the hypothalamus. Also, general anesthetics and muscle relaxants block the shivering response and reduce metabolic heat production. Moreover, the use of cold, dry anesthetic gases increases evaporative heat losses in the lungs, and peripheral vasodilatation makes the patient nearly poikilothermic. In a cool operating room, reduction of a patient's body temperature to 32° to 34° C. (89.6° to 93.2° F.) is not uncommon if preventive measures are not taken. Intraoperative hypothermia is responsible for a reduction in the rate of drug metabolism, an alteration in cerebral and regional blood flow, variations in EEG recordings and increased latency to post-surgical arousal.

In general, body temperature is determined by the balance between heat production and heat loss. Euthermia is maintained by the body's ability to vary heat production and to conserve heat. An anesthetized patient, with a relatively low metabolic rate and minimal control over heat loss, is obviously at a disadvantage. Metabolic heat production in an anesthetized normal adult male is 60–70 kcal per hour. Heat is lost through four parallel pathways: conduction, evaporation, convection, and radiation. Of these, conduction and evaporation cause the fewest intraoperative problems. Conductive loss is minimal (less than 10%) because of the low specific heat and conductivity of conventional drapes and mattresses. Although evaporative heat loss (i.e., insensible perspiration plus evaporation from the respiratory tract) is approximately 25 kcal per hour, this loss can be reduced to 10–15 kcal per hour by using moist warm-inspired gases.

The major causes of heat loss in the operating room are convection and radiation. Convective heat loss is a function of ambient temperature and the square root of air velocity. In a 21° C. operating room, an exposed patient's convective heat loss can be as high as 80 kcal per hour. Conventional surgical draping reduces both the velocity and volume of air interacting with a patient's body and accordingly decreases convective heat loss to about 20 kcal per hour.

The human body is nearly a perfect emitter and absorber at the wavelengths involved in thermal exchange. Since the probability of photon reflection is nearly zero in a typical operating room, radiant heat loss is a function of the difference between the patient's body temperature and the temperature of the operating room. In a 21° C. operating room, a patient's radiant heat loss can be as high as 100 kcal per hour. Accordingly, it is the rate and degree of a patient's radiant heat loss that must be reduced to prevent the onset of intraoperative hypothermia.

Changes in body temperature that lead to intraoperative hypothermia occur more frequently in pediatric patients and carry greater risks than those in adults. A sick infant is unable to maintain thermal stability and dehydration, diarrhea and weakness serve to increase heat loss. Infants on the operating table may lose considerable amounts of heat both by convection into the air-conditioned operating room and by radiation to the cool walls. The resultant low body temperature is one of the most common causes of the stoppage of breathing following general anesthesia. Frequently the infant must be rewarmed before spontaneous respiration resumes. It is therefore essential that an infant in the operating room be kept normothermic.

Unsuspected hypothermia also particularly affects the elderly, whose ability to increase heat production and to decrease heat loss by vasoconstriction in response to cold is impaired. Hypothermia in the elderly is particularly troublesome since it leads to post-anesthetic shivering (PAS). Many complications arise from PAS due to the markedly increased demand on the cardiovascular and pulmonary systems. With age, cardiovascular and pulmonary physiology decline, resulting in less reserve capacity and borderline compensated function. Therefore, particularly in older patients with generally compromised physical condition, additional care must be taken to avoid intraoperative hypothermia and the resultant PAS.

It is therefore apparent that a need exists for a viable method and apparatus for preventing intraoperative hypothermia in all surgical patients. Many different methods and apparatus including pre-warmed gel-filled mattresses, blankets with circulating warm liquid, suits with circulating warm liquid, heating lamps, radiant heaters, humidification of inspired gases and metallized plastic sheeting have been utilized in an attempt to minimize heat loss in patients during surgery.

Heat loss in infants has been conventionally minimized by keeping the infant in an incubator until the last moment, by wrapping all extremities in cotton cast padding, and by exposing as little of the body as possible during induction of anesthesia. The use of warmed, humidified anesthetic gases has also been used in preventing heat loss in infants. Heat has also been supplied by placing a warming mattress just beneath the operating table cover, by increasing the operating room temperature to 24° to 27° C. (75° to 80° F.) or by performing the operation beneath a radiant heater especially when operating on premature infants.

The active methods of warming mentioned above carry the risks of overheating of burning patients while humidification of inspired gases increases the risk of bacterial or viral contamination in the breathing circuit. The use of metallized plastic sheeting is discussed below. As noted above, another conventional method of preventing heat loss in surgical patients has been to raise the ambient temperature in the operating room to 24° to 27° C. Surgeons, however, are most comfortable when the operating room temperature is 18° C. while anesthesiologists prefer a temperature of 22° C. Accordingly, this technique of preventing heat loss in surgical patients has obvious drawbacks.

The use of metallized plastic sheeting to reduce radiant heat loss was reported by Dyde and Lunn in 1970 (Thorax (1970), 25, 355). Dyde and Lunn proposed wrapping the lower half of a patient's body in a blanket of aluminum foil coated with polyethylene in an attempt to reduce heat loss during thoracotomy. Dyde and Lunn had good success in reducing heat loss in patients undergoing relatively short thoracotomy procedures.

Radford and Thurlow (*Br. J. Anaesth.* (1979), 51, 237) later found that the type of metallized plastic sheeting used by Dyde and Lunn was ineffective in the prevention of hypothermia in adult patients studied during neurosurgical operations. They concluded that active warming systems were needed to maintain normothermia in patients undergoing neurosurgical operations.

Radford and Thurlow used a type of metallized plastic sheeting made by Thermos under the name of "Space Blanket". Each blanket consisted of two layers of metallized plastic sheeting separated by an artificial fiber layer. Each patient in the control group wore a cotton gown and was covered by one cotton blanket. Each patient in the study group was additionally wrapped in metallized plastic sheeting. The head and shoulders were left exposed, as was the distal part of any limb with an arterial or venous cannula in place. No active warming system was used.

Radford and Thurlow theorized that a drawback of metallized plastic sheeting is that the infrared reflecting property of the metallic surface is reduced or lost by condensed perspiration. This theory may explain the inconsistencies in the results reported by Dyde and Lunn, and those reported by Radford and Thurlow.

Shortly after the publication of the Radford and Thurlow article one commentator observed that the insulation layer in metallized plastic sheeting is thin and that a breakdown may occur. *Brit. J. Anaesthesia* (1980), 52, 359. The commentator concluded that, if metallized plastic sheeting is used in conjunction with surgical diathermy (the therapeutic use of an oscillating electric current of high frequency to produce local heat in body tissues below the surface) there is a serious risk of burns from aberrant earthing. Thus, the prevailing view was that there was a significant electrical hazard present when space blankets or metallized plastic sheeting was used with diathermy and metal operating tables.

Bourke, D. L. et al. (Intraoperative Heat Conservation Using a Reflective Blanket. *Anesthesiology*, 60: 151–154, 1984) studied the effectiveness of a reflective blanket in reducing radiant heat loss in an anesthetized patient. The reflective blanket used in the Bourke study was aluminized Tyvek, type 1443, which is used as a lining in survival apparel. All patients in the Bourke study were placed on an active heating blanket whose temperature had equilibrated with ambient temperature. The test patients were wrapped in the aluminized blanket as completely as positioning would allow. The blanket utilized in this study was perforated so that it would not trap moisture that could condense and cause skin maceration during prolonged use. The blanket utilized in this study was apparently conductive since a copper cable was used to connect the aluminized blanket to the operating table to prevent patient isolation. Also, as noted above, a perforated aluminized blanket poses a significant electrical hazard in the operating room environment. Thus, the reflective blanket utilized in the Bourke study would appear to pose a significant electrical hazard in the operating room environment.

SUMMARY OF THE INVENTION

The reflective surgical drape of the present invention avoids the above-mentioned disadvantages which are characteristic of the prior art. The reflective surgical drape of the present invention is non-conductive and puncture resistant and therefore poses no electrical hazard in the operating room environment. Certain embodiments of the present invention absorb perspiration to prevent maceration of the skin of the patient and to maintain the infrared reflecting properties of the drape.

The reflective surgical drape of the present invention has utility in reducing a patient's rate of heat loss in any surgical procedure. The drape of the present invention also enhances intraoperative EEG monitoring in neurosurgical patients. The drape also has potential application in neonatal and adult intensive care facilities. The drape may take several forms, including full and partial body length drapes, as well as leggings and caps.

The drape of the present invention comprises a core layer of non-conductive aluminum and a first and second adjacent layer of a thermoplastic material. A non-woven layer of absorbent material is attached to either the first or second adjacent layer of thermoplastic material.

In a preferred embodiment, the drape of the present invention comprises a first layer of non-conductive aluminum and a second layer of a thermoplastic material. A third layer of non-woven absorbent material is attached to the first layer of non-conductive aluminum.

In another preferred embodiment, the drape of the present invention comprises a core layer of non-conductive aluminum and a first and second adjacent layer of a thermoplastic material.

BRIEF DESCRIPTION OF THE DRAWINGS

In describing the invention, reference will be made to the accompanying drawings in which.

DETAILED DESCRIPTION OF THE PREFERRED EMBODIMENTS

Figure 1:
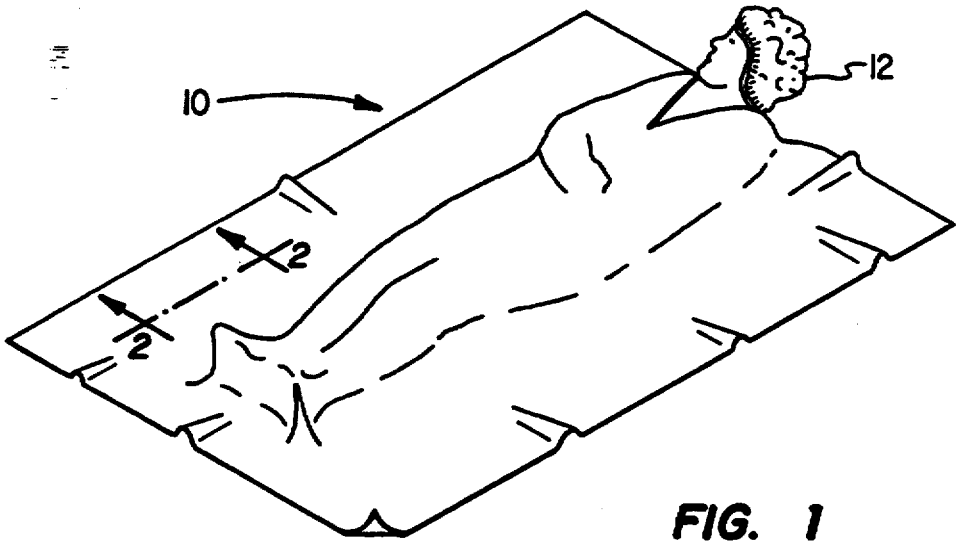
FIG. 1 is a perspective view of the reflective surgical draping of the present invention.
Figure 3:
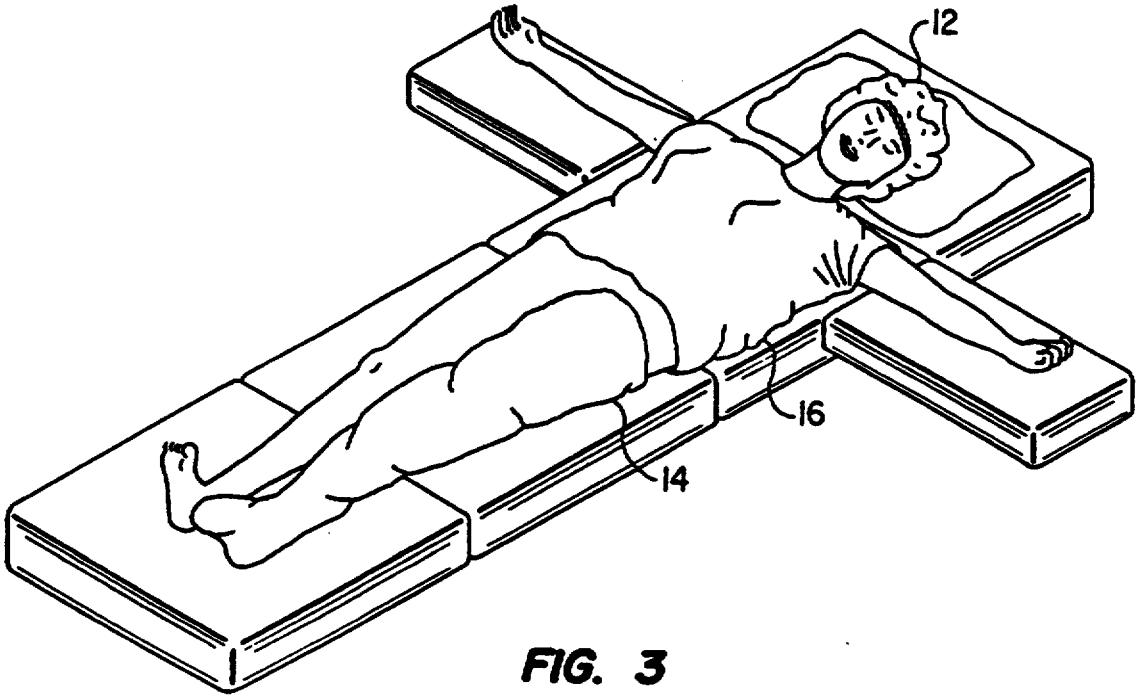
FIG. 3 is a perspective view showing various forms of the reflective surgical draping of the present invention covering the left leg, torso and head of a human patent.

Referring now to the drawings, and in particular FIG. 1, a reflective surgical drape generally indicated at 10 is used for covering a surgical patient and reducing heat loss from the patient's body during a surgical procedure. As shown in FIG. 1, the reflective surgical drape 10 may be fashioned as a blanket which may be wrapped closely about a portion or the entire body of a patient undergoing a surgical procedure. As shown in FIGS. 1 and 3 the reflective surgical drape may be fashioned as a cap 12 which serves as a head covering for a surgical patient. Those skilled in the art will recognize that the cap may be provided with a peripheral elastic band or other means to ensure the cap remains on the patient's head. Also as shown in FIG. 3, the reflective surgical drape may be fashioned as leggings 14 which comprise an open end for receiving a patient's leg and an opposite closed end. Additionally, as shown in FIG. 3 the reflective surgical drape may be fashioned as a covering 16 for the torso of a patient undergoing a surgical procedure. Those skilled in the art will recognize that the reflective surgical drape may be fashioned in any desired conformation to cover any selected portion of the body of a patient undergoing a surgical procedure.

Figure 2:
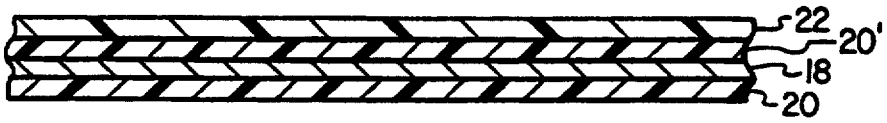
FIG. 2 is a section taken along line 2—2 of FIG. 1.

As shown in FIG. 2, one embodiment of the drape 10 of the present invention is a four layer drape wherein a core layer 18 comprises non-conductive aluminum and a first and second adjacent layer 20,20' comprise a thermoplastic material. A non-woven layer of absorbent material 22 is attached to the second adjacent layer 20'. Those skilled in the art will recognize that the non-woven layer of absorbent material 22 may be attached to either the first or second adjacent layer 20,20'. Preferably, the core layer 18 of non-conductive aluminum is vacuum deposited on the first adjacent layer 20 of thermoplastic material. The core layer 18 of non-conductive aluminum is a vacuum deposit of aluminum preferably having a thickness of from 270 Å to 330 Å and most preferably a thickness of approximately 300 Å. The core layer 18 of non-conductive aluminum is preferably substantially enclosed or sandwiched between the first and second adjacent layers 20,20' of thermoplastic material. The second adjacent layer 20' of thermoplastic material is preferably laminated to the vacuum deposited core layer 18 of non-conductive aluminum using an adhesive. The adhesive is preferably moisture-proof and is most preferably an acrylic moisture-proof adhesive. Alternatively, the second adjacent layer 20' of thermoplastic material is preferably heat extruded to the vacuum deposited core layer 18 of non-conductive aluminum.

The thermoplastic material of the first and second adjacent layers 20,20' must be flexible but need not be transparent. The thermoplastic material of the first and second adjacent layers 20,20' may, preferably, be low-density polyethylene, medium-density polyethylene, polypropylene, polyester or polybutylene. The thermoplastic material of the first and second adjacent layers 20,20', most preferably, is low-density polyethylene. Those skilled in the art will recognize, however, that other flexible thermoplastic materials may be used as the thermoplastic material of the first and second adjacent layer 20,20'. The first and second adjacent layers 20,20' preferably have a thickness of from 0.00120 to 0.00130 mils and most preferably have a thickness of 0.00125 mils. The thermoplastic material of the first and second adjacent layers 20,20' aids in the retention and reflection of body heat and provides puncture resistance to the drape.

The non-woven layer of absorbent material 22 may be attached to the first or second adjacent layer 20,20'. The non-woven layer of absorbent material 22 must be able to absorb modest amounts of perspiration so as to not reduce the infrared reflecting properties of the drape. The non-woven layer of absorbent material 22 may accordingly be one or a blend of cotton, polyester, rayon, polypropylene or cellulose. The non-woven layer of absorbent material 22 preferably has a thickness of from 0.0015 to 0.040 mils and most preferably has a thickness of 0.014 to 0.016 mils. The non-woven layer 22 is preferably attached to the first or second adjacent layer 20,20' using an adhesive. The adhesive is preferably moisture-proof and is most preferably an acrylic moisture-proof adhesive. The non-woven layer of absorbent material 22 absorbs perspiration to prevent maceration of the skin of the patient and provides general comfort to the patient.

In a preferred embodiment of the present invention, the second adjacent layer 20' is omitted and the non-woven layer of absorbent material 22 is attached to the core layer 18 of non-conductive aluminum. The non-woven layer of absorbent material 22 is preferably attached to the core layer 18 of non-conductive aluminum using an adhesive. The adhesive is preferably moisture-proof and is most preferably an acrylic moisture-proof adhesive.

In another preferred embodiment of the present invention, the non-woven layer of absorbent material 22 is omitted. In this embodiment, the surgical drape of the present invention comprises the core layer 18 of non-conductive aluminum and the first and second adjacent layers 20,20'.

The reflective surgical drape of the present invention was tested for conductivity. The tests conducted utilized both 60 cycle per second current (Line Power) and radio frequency current (Electrosurgical Power). Contact to the material was made with standard monitoring electrodes as well as by mechanically abrading the surface of the material. At 120 volts 60 cycle per second the resistance was determined to be in excess of 1 megaohm and well within the range of safety. At frequencies common to electrosurgery units it was determined that the material passed less than 1/10 the current (or 1/100 the power) that would pass through a patient at a maximum power of over 100 watts R.F. from an electrosurgical generator. This test simulated a worst case scenario of applying a cutting electrode directly to the reflective surgical drape. The inability of the reflective surgical drape of the present invention to conduct current is attributable to the layer of aluminum that is vacuum deposited on the thermoplastic layer. The aluminum layer would need to be many times thicker to perform as a conductor in a significant manner. These tests indicate that the reflective surgical drape of the present invention poses no problem when used in the presence of Line Voltage or Electrosurgical Generators.

The reflective surgical drape of the present invention provides many safety features, the most important of which are its nonconductivity and its resistance to puncture. The drape is also inert to alcohol and betadine which insures that the drape maintains its integrity throughout a surgical procedure. The non-woven layer of absorbent material also absorbs perspiration to prevent maceration of the skin of the patient and to maintain the infrared reflecting properties of the drape.

EXAMPLE 1

Patients admitted for elective neurological, maxillofacial, gynecological and urological surgery were randomly assigned to treatment or control groups. Control group patients were draped in a conventional manner for the surgical procedure. Treatment group patients were draped in the same manner with the addition of the reflective surgical drape of the present invention placed closest to the patient prior to standard draping. All other treatment of the two groups was similar.

The body temperature of each patient was systematically recorded with an oropharyngeal thermistor probe placed immediately after induction of general anesthesia.

Neurological and maxillofacial patients designated Group A were draped with a full length section (shoulder to foot) of the reflective surgical drape of the present invention while urologic and gynecologic patients designated Group B were draped with a half sheet section (upper chest/abdomen) and leggings made of the reflective surgical drape of the present invention.

The induction temperature for both treatment and control groups was similar (approximately 36.5° C., $p>0.5$). The average duration of surgery for Group A patients was 1.75 hours, while the average duration of surgery for Group B patients was 7.5 hours.

The recorded temperature at the end of the procedure for Group A patients was 37.2±0.6 for treatment patients and 35.0±0.5 for control patients ($p<0.01$).

The recorded temperature at the end of the procedure for Group B patients was 35.9°±0.3° C. for treatment patients and 34.7°±0.5° C. for control patients ($p<0.01$).

Group A and B control group patients experienced temperature decreases of an average of 1.6° to 1.8° C. which was statistically significant. Group A and B treatment group patients experienced temperature decreases averaging 0.4° C., which was not statistically significant.

Figure 5:
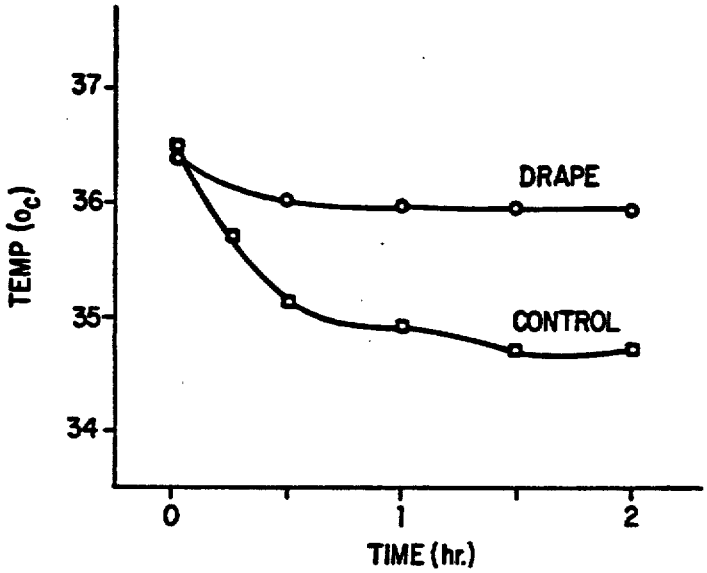
FIG. 5 is a plot of temperature versus time for patients undergoing urological or gynecological surgery.
Figure 4:
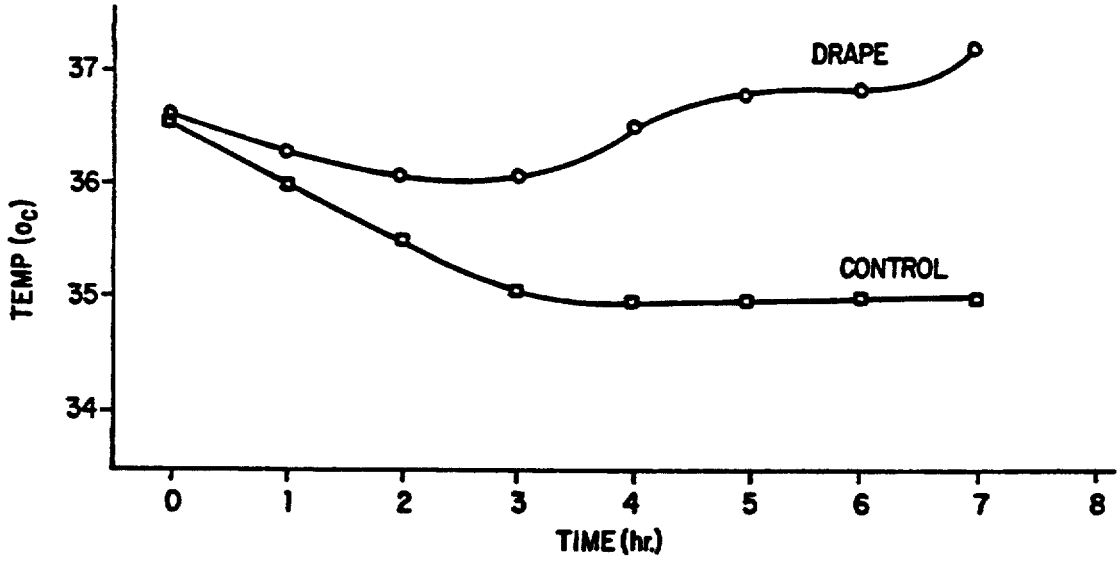
FIG. 4 is a plot of temperature versus time for patients undergoing neurological and maxillofacial surgery.

The results for Group A and B patients are found in Table I below and are shown graphically in FIGS. 4 and 5, respectively.

TABLE 1

| | Temp | | |
|---|---|---|---|
| | Starting | Ending | |
| Group A (Neurological, maxillofacial) | | | |
| With drape | 36.6 ± 0.3 | 37.2 ± 0.6 | (n = 20) |
| Without drape | 36.6 ± 0.4 | 35.0 ± 0.5* | (n = 20) |
| Group B (Gynecological, urological) | | | |
| With drape | 36.4 ± 0.4 | 35.9 ± 0.3 | (n = 20) |
| Without drape | 36.5 ± 0.3 | 34.7 ± 0.5* | (n = 20) |

*Statistically significant difference from starting temperature ($p < 0.01$).

One can conclude from these results that patients who were draped with the reflective surgical material of the present invention developed significantly less reduction in oropharyngeal temperature compared to control patients.

In fact, in the majority of neurosurgical procedures in which the patient was draped with the reflective surgical drape of the present invention all other warming devices (i.e. humidifier, heating pads, warmed intravenous fluids) standardly used were discontinued due to maintenance of normal body temperature with the reflective surgical drape alone.

No adverse effects were noted in any case in which the reflective drape material was used.

While the present invention has been described in detail and with reference to specific examples thereof, it will be apparent to one skilled in the art that various changes and modifications can be made therein without departing from the spirit and scope thereof.

What is claimed is:

1. A reflective surgical drape for covering a surgical patient and reducing heat loss from the patient's body during and after a surgical procedure, comprising:

(a) [a] *an electrically* non-conductive core layer of aluminum;

(b) a first and second adjacent layer of a thermoplastic material; and (c) a non-woven layer of absorbent material attached to said first adjacent layer;

*wherein said drape is non-perforated.*

2. A reflective surgical drape according to claim 1, wherein said non-conductive core layer of aluminum is vacuum deposited to said first adjacent layer of a thermoplastic material.

3. A reflective surgical drape according to claim 2, wherein said vacuum deposited non-conductive core layer of aluminum has a thickness of from 270 Å to 330 Å.

4. A reflective surgical drape according to claim 3, wherein said vacuum deposited non-conductive core layer of aluminum has a thickness of 300 Å.

5. A reflective surgical drape according to claim 1, wherein said thermoplastic material of said first adjacent layer and said second adjacent layer is selected from the group consisting of low-density polyethylene, medium-density polyethylene, polypropylene, polyester or polybutylene.

6. A reflective surgical drape according to claim 5, wherein said thermoplastic material of said first adjacent layer and said second adjacent layer is low-density polyethylene.

7. A reflective surgical drape according to claim 1, wherein said first adjacent layer and said second adjacent layer each have a thickness of from 0.00120 to 0.00130 mils.

8. A reflective surgical drape according to claim 7, wherein said first adjacent layer and said second adjacent layer each have a thickness of 0.00125 mils.

9. A reflective surgical drape according to claim 2, wherein said second adjacent layer of a thermoplastic material is laminated with an adhesive to said non-conductive core layer of aluminum.

10. A reflective surgical drape according to claim 9, wherein said adhesive is acrylic and moisture proof.

11. A reflective surgical drape according to claim 1, wherein said non-woven layer of absorbent material is one or a blend of cotton, polyester, rayon, polypropylene or cellulose.

12. A reflective surgical drape according to claim 11, wherein said non-woven layer has a thickness of from 0.0015 to 0.040 mils.

13. A reflective surgical drape according to claim 12, wherein said non-woven layer has a thickness of from 0.014 to 0.016 mils.

14. A reflective surgical drape according to claim 11, wherein said non-woven layer of absorbent material is attached with a adhesive to said first adjacent layer.

15. A reflective surgical drape according to claim 14, wherein said adhesive is acrylic and moisture proof.

16. A reflective surgical drape according to claim 1, wherein a selected length of said drape is fashioned to be closely received about at least a portion of the body of the patient during the surgical procedure.

17. A reflective surgical drape according to claim 16, wherein said selected length of said drape is fashioned as a blanket which is wrapped closely about the torso of a patient undergoing a surgical procedure.

18. A reflective surgical drape according to claim 16, wherein said selected length of said drape is fashioned as a cap which serves as a head covering for a patient undergoing a surgical procedure.

19. A reflective surgical drape according to claim 16, wherein said selected length of said drape is fashioned as a limb covering for a patient undergoing a surgical procedure, said limb covering comprising a cylindrically-shaped length of said drape having an open end for receiving the patient's limb and an opposite closed end.

20. A reflective surgical drape for covering a surgical patient and reducing heat loss from the patient's body during and after a surgical procedure, comprising:

(a) [a] *an electrically* non-conductive first layer of aluminum;

(b) a second layer of a thermoplastic material attached to said non-conductive first layer of aluminum; and (c) a third layer of non-woven absorbent material attached to said non-conductive first layer of aluminum;

*wherein said drape is non-perforated.*

21. A reflective surgical drape according to claim 20, wherein said non-conductive first layer of aluminum is vacuum deposited to said second layer of a thermoplastic material.

22. A reflective surgical drape according to claim 21, wherein said vacuum deposited non-conductive layer of aluminum has a thickness of from 270 Å to 330 Å.

23. A reflective surgical drape according to claim 22, wherein said vacuum deposited non-conductive layer of aluminum has a thickness of 300 Å.

24. A reflective surgical drape according to claim 20, wherein said thermoplastic material of said second layer is selected from the group consisting of low-density polyethylene, medium-density polyethylene, polypropylene, polyester or polybutylene.

25. A reflective surgical drape according to claim 24, wherein said thermoplastic material of said second layer is low-density polyethylene.

26. A reflective surgical drape according to claim 20, wherein said second layer has a thickness of from 0.00120 to 0.00130 mils.

27. A reflective surgical drape according to claim 26, wherein said second layer has a thickness of 0.00125 mils.

28. A reflective surgical drape according to claim 20, wherein said non-woven layer of absorbent material is one or a blend of cotton, polyester, rayon, polypropylene or cellulose.

29. A reflective surgical drape according to claim 28, wherein said non-woven layer has a thickness of from 0.0015 to 0.040 mils.

30. A reflective surgical drape according to claim 29, wherein said non-woven layer has a thickness of from 0.014 to 0.016 mils.

31. A reflective surgical drape according to claim 28, wherein said non-woven layer of absorbent material is attached with an adhesive to said second layer of a thermoplastic material.

32. A reflective surgical drape according to claim 31, wherein said adhesive is acrylic and moisture-proof.

33. A reflective surgical drape for covering a surgical patient and reducing heat loss from the patient's body during and after a surgical procedure, comprising:

(a) [a] *an electrically* non-conductive first layer of aluminum;

(b) a second layer of a thermoplastic material attached to said non-conductive first layer of aluminum; and (c) a third layer of non-woven absorbent material attached to said non-conductive first layer of aluminum;

wherein said reflective surgical drape has a resistance of at least one megaohm;

*and wherein said drape is nonperforated.*

*34. A reflective surgical drape for covering a surgical patient and reducing heat loss from the patient's body during and after a surgical procedure, comprising:*

*(a) an electrically non-conductive core layer of aluminum;*

*(b) a first and second adjacent layer of a thermoplastic material; and*

*(c) a non-woven layer of absorbent material attached to said first adjacent layer;*

*wherein said non-woven layer of absorbent material is attached with an adhesive to said first adjacent layer of a thermoplastic material.*

*35. A reflective surgical drape for covering a surgical patient and reducing heat loss from the patient's body during and after a surgical procedure, comprising:*

*(a) an electrically non-conductive first layer of aluminum;*

*(b) a second layer of a thermoplastic material attached to said non-conductive first layer of aluminum; and*

*(c) a third layer of non-woven absorbent material attached to said non-conductive first layer of aluminum;*

*wherein said layer of non-woven absorbent material is attached with an adhesive to said layer of aluminum.*

*36. A reflective surgical drape for covering a surgical patient and reducing heat loss from the patient's body during and after a surgical procedure, comprising:*

*(a) an electrically non-conductive first layer of aluminum;*

*(b) a second layer of a thermoplastic material attached to said non-conductive first layer of aluminum; and*

*(c) a third layer of non-woven absorbent material attached to said non-conductive first layer of aluminum;*

*wherein said reflective surgical drape has a resistance of at least one megaohm;*

*and wherein said non-woven layer of absorbent material is attached with an adhesive to said first adjacent layer of a thermoplastic material.*

*37. A reflective surgical drape for covering a surgical patient and reducing heat loss from the patient's body during and after a surgical procedure, consisting of:*

*(a) an electrically non-conductive core layer of aluminum;*

*(b) a first and second adjacent layer of a thermoplastic material; and*

*(c) a non-woven layer of absorbent material attached to said first adjacent layer.*

*38. A reflective surgical drape for covering a surgical patient and reducing heat loss from the patient's body during and after a surgical procedure, consisting of:*

*(a) an electrically non-conductive first layer of aluminum;*

*(b) a second layer of a thermoplastic material integrally attached to said non-conductive first layer of aluminum; and*

*(c) a third layer of non-woven absorbent material integrally attached to said non-conductive first layer of aluminum.*

*39. A reflective surgical drape for covering a surgical patient and reducing heat loss from the patient's body during and after a surgical procedure, consisting of:*

*(a) an electrically non-conductive first layer of aluminum;*

*(b) a second layer of a thermoplastic material attached to said non-conductive first layer of aluminum; and*

*(c) a third layer of non-woven absorbent material attached to said non-conductive first layer of aluminum;*

*wherein said reflective surgical drape has a resistance of at least one megaohm.*

* * * * *